US00PP28740P3

(12) United States Plant Patent
Giesen

(10) Patent No.: US PP28,740 P3
(45) Date of Patent: Dec. 5, 2017

(54) ***DAHLIA* PLANT NAMED 'DAHZ0004'**

(50) Latin Name: ***Dahlia* hybrid Cav.**
Varietal Denomination: DAHZ0004

(71) Applicant: SYNGENTA PARTICIPATIONS AG, Basel (CH)

(72) Inventor: Eric Giesen, Andijk (NL)

(73) Assignee: Syngenta Participations AG, Basel (CH)

( * ) Notice: Subject to any disclaimer, the term of this patent is extended or adjusted under 35 U.S.C. 154(b) by 102 days.

(21) Appl. No.: 14/757,270

(22) Filed: Dec. 10, 2015

(65) Prior Publication Data

US 2016/0205857 P1 Jul. 14, 2016

Related U.S. Application Data

(60) Provisional application No. 62/102,271, filed on Jan. 12, 2015.

(51) Int. Cl.
*A01H 5/02* (2006.01)

(52) U.S. Cl.
USPC ..... Plt./321

(58) Field of Classification Search
USPC ..... Plt./263.1, 321
See application file for complete search history.

*Primary Examiner* — Susan McCormick Ewoldt
*Assistant Examiner* — Karen Redden
(74) *Attorney, Agent, or Firm* — Dale Skalla

(57) ABSTRACT

A new *Dahlia* plant named 'DAHZ0004', particularly distinguished by the large pink, double-type flowers, an upright plant habit with good branching, dark green foliage, and good floriferousness.

1 Drawing Sheet

Latin name of the genus and species of the plant claimed: *Dahlia* hybrid Cav.

Varietal denomination: 'DAHZ0004'.

BACKGROUND OF THE NEW PLANT

The present invention comprises a new *Dahlia*, botanically known as *Dahlia* hybrid and hereinafter referred to by the variety name 'DAHZ0004'.

'DAHZ0004' is a product of a planned breeding program. The new cultivar has large pink double flowers, an upright plant habit with good branching, dark green foliage, and good floriferousness.

'DAHZ0004' originates from a sibling cross hybridization in a controlled breeding program in Andijk, Netherlands. The pollinations were made in May 2007.

The female parent was an unpatented, proprietary hybrid seedling identified as 'D06-262-1', having light pink flower color, medium green foliage and a larger plant size than 'DAHZ0004'.

The male parent of 'DAHZ0004' was an unpatented, proprietary plant identified as 'D06-262-4', with rose flower color, large flower size, dark green leaves, and an open and less branching plant habit than 'DAHZ0004'.

The resulting the seed sown in April 2008 and 'DAHZ0004' was selected as one flowering plant within the progeny of the stated cross in September 2008 in a greenhouse in Andijk, Netherlands.

The first act of asexual reproduction of 'DAHZ0004' was accomplished when vegetative cuttings were propagated from the initial selection in April 2009 in a controlled environment in Andijk, Netherlands.

BRIEF SUMMARY OF INVENTION

Horticultural examination of plants grown from cuttings of the plant initiated in May 2013 in Andijk, Netherlands, and continuing thereafter, has demonstrated that the combination of characteristics as herein disclosed for 'DAHZ0004' are firmly fixed and are retained through successive generations of asexual reproduction.

'DAHZ0004' has not been observed under all possible environmental conditions. The phenotype may vary significantly with variations in environment such as temperature, light intensity and day length.

A Plant Breeder's Right for this cultivar has not yet been applied for. 'DAHZ0004' has not been made publicly available more than one year prior to the filing of this application.

The following traits have been repeatedly observed and are determined to be basic characteristics of the new variety. The combination of these characteristics distinguishes this *Dahlia* as a new and distinct variety.

BRIEF DESCRIPTION OF THE PHOTOGRAPH

The accompanying photographic drawing shows typical flower and foliage characteristics of 'DAHZ0004' with colors being as true as possible with an illustration of this type.

The photographic drawing shows in FIG. 1 a close-up of the flowers.

DETAILED BOTANICAL DESCRIPTION

The aforementioned photograph was taken in May 2013 in Andijk, Netherlands. The plants were growing in 13 cm pots on benches in a greenhouse. They were about 14 weeks of age.

The plant descriptions and measurements were taken in Enkhuizen, The Netherlands on September 4, 2014 from 14 week old plants that were growing outdoors in the trial field.

Color references are made to The Royal Horticultural Society Colour Chart (R.H.S.) 2001.

TABLE 1

DIFFERENCES BETWEEN THE NEW VARIETY 'DAHZ0004' AND A SIMILAR VARIETY

| | 'DAHZ0004' | 'Dahlia XXL Chiapas', not patented |
|---|---|---|
| Overall flower color: | Bright Pink | Lavender Pink |
| Flower type or position: | Medium large, double flower | Large flower. |
| Foliage: | Dark green | Medium dark green |
| Plant size or habit: | Medium large plant with medium long flower stems | Large plant with short flower stems |

Plant:

*Form, growth and habit.*—Semi-upright, tight and compact; freely branching.

*Plant height.*—27 cm.

*Plant height (inflorescence included).*—39 cm.

*Plant width.*—40 cm.

*Garden performance and tolerance to weather.*—Good.

*Crop time to flowering.*—About 9-12 weeks.

Roots:

*Number of days to initiate and develop roots.*—About 21-28 days at about 21 degrees C.

*Type.*—Fine, fibrous, free branching.

*Color.*—RHS N155B but whiter.

Foliage:

*Arrangement.*—Opposite, single, simple and sometimes pinnate.

*Immature, leaf color, upper surface.*—Between RHS 137B.

*Lower surface.*—RHS 138B to RHS 138C.

*Mature, leaf color, upper surface.*—RHS 147B.

*Lower surface.*—RHS 138B but slightly more greyish.

*Type.*—Mostly simple, some are pinnate.

*Length.*—11 cm, including petiole.

*Width.*—8-9 cm.

*Shape.*—Ovate to deltoid for the pinnate.

*Base shape.*—Pinnate leaves are truncate, simple leaves are acute.

*Apex shape.*—Acute to obtuse.

*Margin.*—Dentate.

*Texture, upper surface.*—Little hairy on the edges, slightly glossy.

*Lower surface.*—Some lonely hair on the main vein.

*Venation color, upper.*—RHS 143B.

*Lower.*—RHS 143D.

*Petiole color.*—RHS 144C.

*Petiole length.*—1-4 cm.

*Diameter of petiole.*—0.3 cm at the mid-section.

*Texture.*—Glabrous.

Stem:

*Average quantity of main branches per plant.*—About 5 to 6 that are divided in 3 branches.

*Color of stem.*—RHS 144B-C.

*Length of stem.*—25 cm.

*Diameter.*—0.6 cm at the midsection.

*Length of internodes.*—5.5-8.5 cm.

*Texture.*—Glabrous.

*Color of peduncle.*—RHS N144D.

*Length of peduncle.*—6-10 cm.

*Peduncle diameter.*—0.2-0.3 cm.

*Texture.*—Glabrous.

Inflorescence:

*Type.*—Inflorescences borne on terminals above foliage; daisy-eyed double.

*Blooming habit.*—Continuous throughout the growing season.

*Average quantity of inflorescences per plant.*—70, with buds.

*Average quantity of inflorescences per lateral stem.*—10-13.

*Lastingness of individual blooms on the plant.*—7-12 days.

*Fragrance.*—None.

Bud (just before opening):

*Color.*—RHS N74D on the top, to greener at the base: RHS 144B.

*Length.*—1.5 cm.

*Width.*—1.7 cm.

*Shape.*—Completely round to bell-shaped with unfolding of the rays.

Immature inflorescence:

*Diameter.*—About 5.5 cm.

*Color of ray florets, upper surface.*—RHS 75D.

*Lower surface.*—RHS N74C.

Mature inflorescence:

*Diameter.*—7.5-9 cm.

*Depth.*—4 cm.

*Total diameter of 'disc'.*—1-1.2 cm.

*Recepticle height.*—0.2 cm.

*Recepticle diameter.*—1.4-1.5 cm.

Ray florets:

*Average quantity of florets.*—About 70, disposed in few layers.

*Color of florets, upper surface.*—RHS 75B.

*Lower surface.*—RHS 75A.

*Length.*—3.0 -3.2 cm.

*Width.*—1.4 cm.

*Shape.*—Broadly elliptical.

*Base shape.*—Rolled to fused just at the base, acute.

*Apex shape.*—Mucronulate.

*Margin.*—Entire.

*Texture, upper surface.*—Papillose; glabrous.

*Lower surface.*—Papillose; single hairs along the veins.

*Number of petaloids.*—2-3 per ray floret.

*Color of petaloids, upper surface.*—As the petals, deeper than RHS 75B.

*Lower surface.*—RHS 75A.

*Length.*—0.5-1 cm.

*Width.*—0.2-0.4 cm.

*Shape.*—Strongly involute and sometimes twisted.

*Apex shape.*—Rounded to acute.

Disc florets:

*Average quantity of florets.*—About 65-75 quantity.

*Color of florets.*—RHS N74C.

*Length.*—0.6-0.9 cm.

*Width.*—0.25 cm.

*Shape.*—Tube-shaped.

*Apex shape.*—Acute, 5-pointed.

Phyllaries:

*Types of phyllaries 2 types.*—Phyllaries are arranged in 2-3 whorls.

*Phyllaries of lower whorl are green and thicker.*—

*Average quantity.*—About 5-7.

*Color, upper surface.*—RHS 147B.

*Lower surface.*—RHS 147B.

*Length.*—1.0 cm.

*Width.*—0.6 cm.

*Shape.*—Ovate.
*Base shape.*—Shortly attenuate.
*Apex shape.*—Acuminate.
*Margins.*—Entire.
*Texture, upper surface.*—Glabrous (no hair).
*Lower surface.*—Glabrous.
*Phyllaries in the upper whorl are mostly transparent.*—
*Average quantity.*—About 10.
*Color, upper surface.*—RHS 154B to RHS 154C.
*Lower surface.*—RHS 154C to RHS 154D.
*Length.*—1.6 cm.
*Width.*—0.5 cm.
*Shape.*—Ligulate.
*Base shape.*—Fused.
*Apex shape.*—Obtuse.
*Margins.*—Entire.
*Texture, upper surface.*—Glabrous (no hair).
*Lower surface.*—Glabrous.

Reproductive organs:
*Gyneocium.*—Present on both ray and disc.
*Pistil quantity.*—1 per floret.
*Length.*—0.8-0.9 cm.
*Style color.*—RHS 154A.
*Style length.*—0.5-0.6 cm.
*Stigma color.*—RHS 13A.
*Stigma shape.*—Bi-furchate (bi-lobed).
*Ovary color.*—RHS 145B.
*Andreocium.*—Present on disc florets only.
*Stamens quantity.*—5 united.
*Color of filaments.*—RHS 150B.
*Length filaments.*—0.3 cm.
*Anther color.*—RHS 17A.
*Anther length.*—0.4 cm.
*Color of pollen.*—RHS 17A.
*Pollen amount.*—Very moderate.
*Fertility/seed set.*—Not observed on this hybrid.

Disease/pest resistance: Disease resistance or susceptibility has not been observed on this hybrid.

What is claimed is:

1. A new and distinct variety of *Dahlia* plant named 'DAHZ0004', substantially as illustrated and described herein.

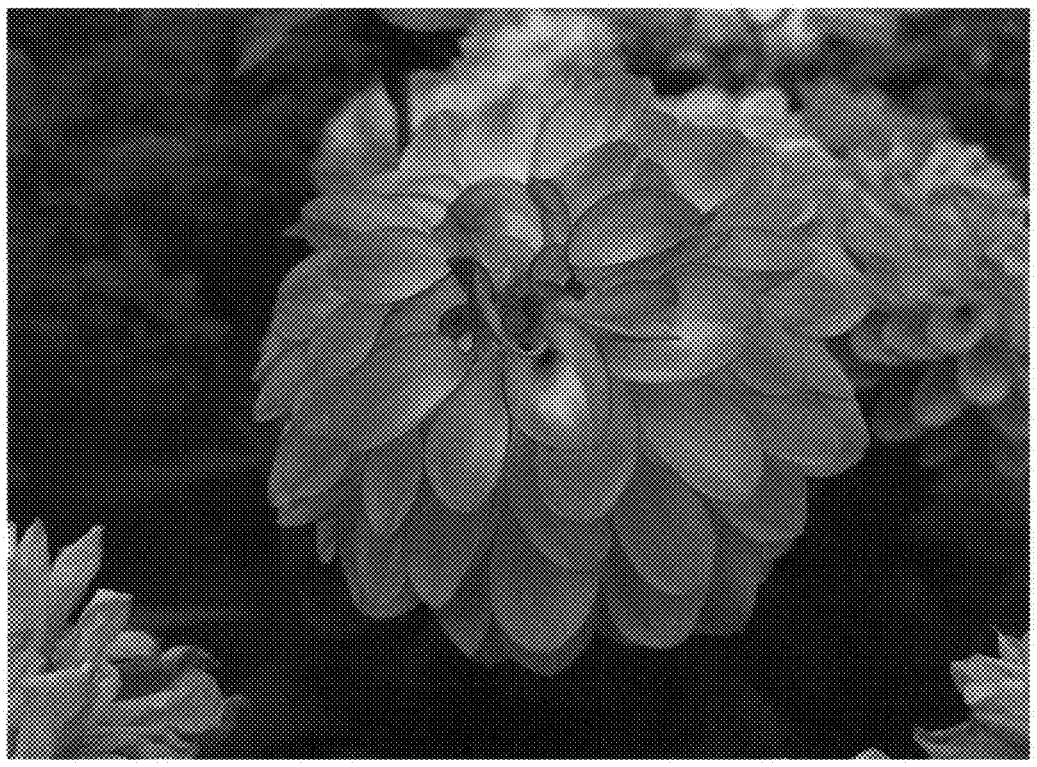

* * * * *